US00PP11637P

United States Patent [19]

Noodelijk

[11] Patent Number: Plant 11,637

[45] Date of Patent: Nov. 14, 2000

[54] CHRYSANTHEMUM PLANT NAMED 'ODYSSEUS'

[75] Inventor: Robert Noodelijk, Woubrugge, Netherlands

[73] Assignee: Chrysanthemum Breeders Association N.V., Netherlands

[21] Appl. No.: 09/179,451

[22] Filed: Oct. 27, 1998

[51] Int. Cl.[7] ..... A01H 5/00

[52] U.S. Cl. ..... Plt./288

[58] Field of Search ..... Plt./288, 287, 289

[56] References Cited

U.S. PATENT DOCUMENTS

| | | | |
|---|---|---|---|
| P.P. 6,402 | 11/1988 | Mack et al. | Plt./288 |
| P.P. 7,517 | 5/1991 | VandenBerg | Plt./288 |
| P.P. 8,294 | 7/1993 | VandenBerg | Plt./288 |

*Primary Examiner*—Howard J. Locker
*Attorney, Agent, or Firm*—Parkhurst & Wendel, LLP

[57] ABSTRACT

A chrysanthemum plant named Odysseus characterized by its medium sized blooms with white ray florets and light yellow to almost white center and mounding prolific branching; natural season flower date of August 24–25; blooming for a period of 7 weeks.

2 Drawing Sheets

BACKGROUND OF THE INVENTION

The new plant of the present invention comprises a new and distinct cultivar of chrysanthemum plant that is a cross of unknown *Dendranthema grandiflora* parents. The new and distinct cultivar was a seedling resulting from the open pollination among groups of chrysanthemum cultivars maintained under the control of the inventor for breeding purposes. The new and distinct cultivar was discovered and selected as one flowering plant by Rob Noodelijk on a cultivated field in Rijsenhout, Holland in August 1996. The plant has been asexually reproduced by cuttings in greenhouses at Rijsenhout, Holland. The new cultivar has been found to retain its distinctive characteristics through successive propagations.

SUMMARY OF THE INVENTION

The present invention is a new and distinct variety of chrysanthemum of a medium sized bloom and white color.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
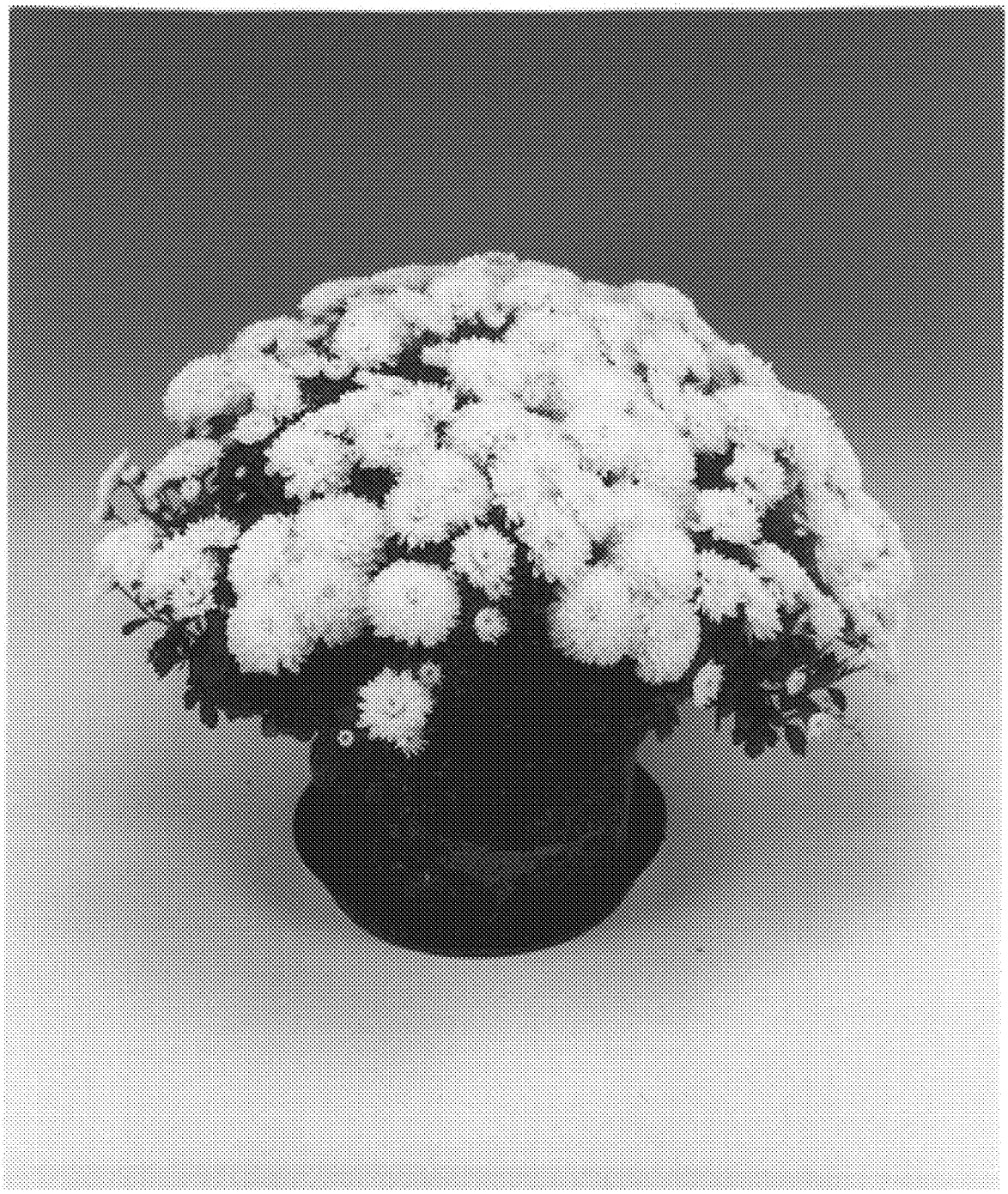
FIG. 1 shows a plant of the cultivar in full bloom.
Figure 2:
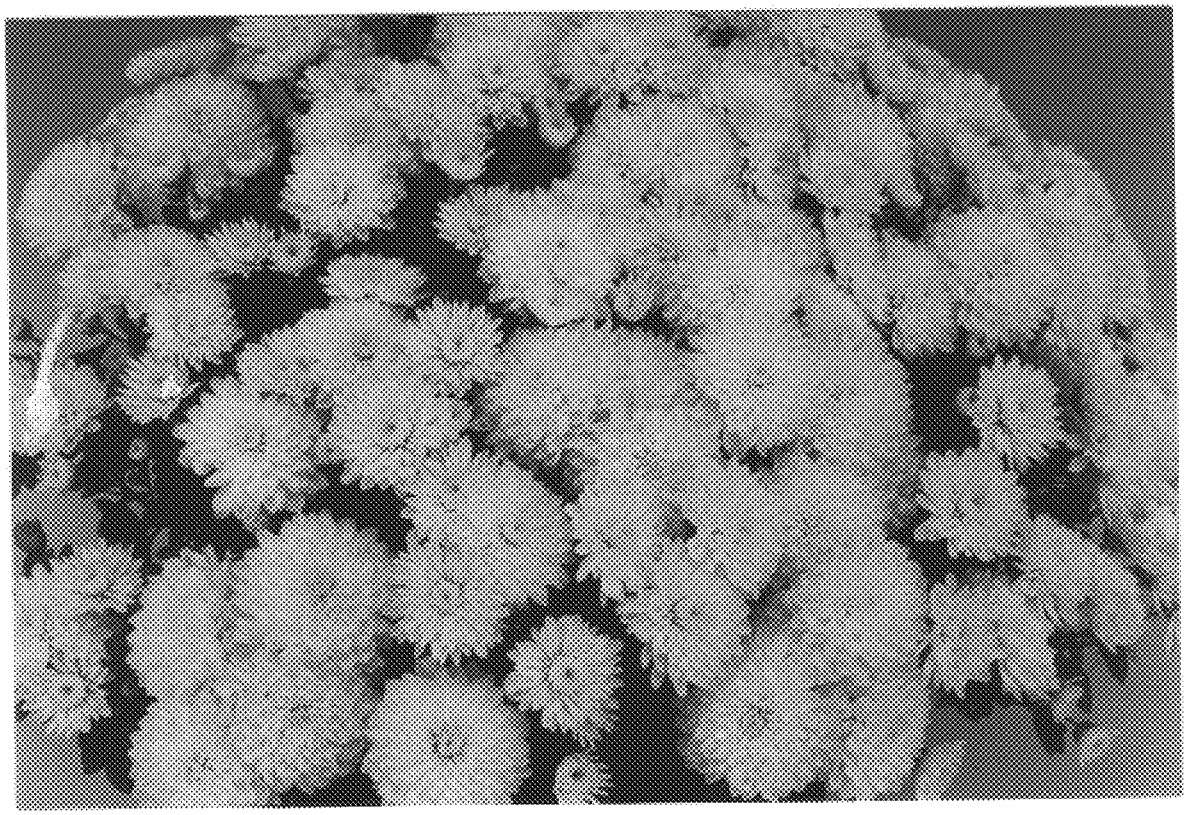
FIG. 2 shows the various stages of bloom of the new cultivar.

This new variety of chrysanthemum is of the botanical classification *Dendranthema grandiflora.*

The observations and measurements were gathered from plants grown outdoors in Rijsenhout, Holland under natural day length and temperature and planted week 22 in 1997 and 1998. The natural blooming date of this crop was August 24–25 (week 34). The average height of the plants was 25 to 28 cms. This new variety produces medium sized blooms with white ray florets and a light yellow to almost white center blooming for a period of 7 weeks. The following is a description of the plant and characteristics that distinguish Odysseus as a new and distinct variety. The color designations (color designations are from the R.H.S. Colour Chart) are taken from the plant itself. Accordingly, any discrepancies between the color designations and the colors depicted in the photographs are due to photographic tolerances.

Of the commercial varieties known to inventor most similar to Odysseus are the varieties Encore, described in U.S. Plant Pat. No. 6,402 and Nicole, described in U.S. Plant Pat. No. 7,517. Odysseus has a much more mounding and prolific branching pattern than either Encore or Nicole. In addition, the flower form and size of Odysseus are different from the flower form and size of Encore and Nicole.

Description of the Plant

Bud:
- *Size.*—Small. Cross section ±1.0 cm. Height ±1.0 cm.
- *Outside color.*—White 155A.

Bloom:
- *Size.*—Medium.
- *Fully Expanded.*—5 cm.
- *Borne* (*number of blooms per branch*).—Upper and lower portion plural blooms per branch (approx. 5–6 blooms).
- *Length of lateral branch.*—From top till the bottom approx. 11.0 cm.
- *Lateral branch, attachment.*—Weak.
- *Branching.*—Mounding and prolific with 8–10 breaks after pinching.
- *Form.*—Decorative.
- *Performance* (*on the plant*).—7 weeks.

Color:
- *Center of flower.*—Near yellow 8 D but more white.
- *Color of the upper surface of the majority of the ray-florets.*—White 155 D.
- *Color of the lower surface of the majority of the ray-florets.*—White 155 D.
- *Tonality from distance.* —A highly floriferous gardenmum with a good mounding habit and white decorative blooms.
- *Discoloration.*—None.
- *Pollen.*—None.

Ray florets:
- *Texture.*—Upperside smooth. Underside smooth.
- *Number.*—±220–250.
- *Cross-section.*—Concave.
- *Longitudinal axis of the majority.*—Incurved.
- *Shape of tip.*—Pointed.

*Fragrance.*—Typical chrysanthemum.
*Disc diameter.*—No disc florets present.

Reproductive organs:
*Stamen.*—Not present.
*Pollen.*—None.
*Styles* (*present in ray florets*).—Green, thin.
*Style length.*—±4 mm.
*Stigmas.*—Yellow-green.
Stigma width.—±1 mm.
*Ovaries.*—Enclosed in calyx.

Plant:
*Form.*—A gardenmum (pot mum) meant for outdoor use.
*Height* (*from soil level*).—25–28 cm.
*Stem color.*—Near green 144 A.
*Stem strength.*—Strong.
*Stem brittleness.*—Present.
*Stem anthocyanin coloration.*—None.

Natural blooming:
*Date.*—August 24–25 (Week 34).

Foliage:
*Color.*—Upperside green 137 A. Underside green 138 B.
*Size.*—Small: Length ±6 cm. Width ±5 cm.
*Quantity* (*number per lateral branch*).—(10–14).
*Shape.*—Incurved.
*Texture.*—Fleshy.
*Ribs and veins.*—Ribs and veins very well developed.
*Edge.*—Crenated.
*Shape of base of sinus between lateral lobes.*—Round.
*Margin of sinus between lateral lobes.*—Converging.
*Shape of base.*—Asymmetric.
*Apex.*—Mucronate.

I claim:

1. A new and distinct variety of chrysanthemum plant as described and illustrated.

* * * * *